(12) United States Patent
Leonhartsberger et al.

(10) Patent No.: US 7,749,756 B2
(45) Date of Patent: Jul. 6, 2010

(54) MICROORGANISM STRAIN FOR PRODUCING RECOMBINANT PROTEINS

(75) Inventors: Susanne Leonhartsberger, Jena (DE); Guenter Wich, Munich (DE)

(73) Assignee: Wacker Chemie AG, Munich (DE)

( * ) Notice: Subject to any disclaimer, the term of this patent is extended or adjusted under 35 U.S.C. 154(b) by 140 days.

(21) Appl. No.: 11/701,725

(22) Filed: Feb. 2, 2007

(65) Prior Publication Data

US 2008/0064062 A1  Mar. 13, 2008

(30) Foreign Application Priority Data

Feb. 2, 2006  (DE) .................. 10 2006 004 871

(51) Int. Cl.
  *C07K 14/00* (2006.01)
(52) U.S. Cl. ..................................... 435/325
(58) Field of Classification Search ................. None
  See application file for complete search history.

(56) References Cited

U.S. PATENT DOCUMENTS

| 5,264,365 | A | 11/1993 | Georgiou et al. |
| 5,830,692 | A | 11/1998 | Bock et al. |
| 2005/0106703 | A1 | 5/2005 | Hashimoto et al. |
| 2006/0073559 | A1 | 4/2006 | Ferrari et al. |
| 2007/0054354 | A1 | 3/2007 | Humphreys et al. |

FOREIGN PATENT DOCUMENTS

| EP | 0 338 410 B1 | 10/1994 |
| EP | 0 677 109 B1 | 4/2000 |
| JP | 08064602 A | 3/1996 |
| JP | 08266291 A | 10/1996 |
| JP | 2005521407 A | 7/2005 |
| JP | 2006502727 A | 1/2006 |
| WO | 98/18946 A1 | 5/1998 |
| WO | WO 00/39323 | 7/2000 |
| WO | WO 03/083125 A1 | 10/2003 |
| WO | 2004/035792 | * 4/2004 |
| WO | 2004/035792 A1 | 4/2004 |
| WO | 2005045006 A | 5/2005 |

OTHER PUBLICATIONS

Westerlund-Wikstrom et al. 1997; Functional expression of adhesive peptides as fusions to *Escherichia coli* flagellin. Protein Engineering 10(11): 1319-1326.*
Mergulhao et al., "Recombinant protein secretion in *Escherichia coli*," Biotechnology Advances, 2005, pp. 177-202, v. 23.
Baneyx et al, "Recombinant protein expression in *Escherida coli*," Current Opinion in Biotechnology, 1999, pp. 411-421, v. 10.
Yasunori, T. et al., "Effect of OmpA Signal Peptide Mutations on OmpA Secretion, , Synthesis, and Assembly," Journal of Bacteriology, Mar. 1991, pp. 1997-2005, v. 173, n. 6.
Wan et al., "TolAlll Co-overexpression Facilitates the Recovery of Periplasmic Recombinant Proteins into the Growth Medium of *Escherichia coli*," Protein Expression and Purification, 1998, pp. 13-22, v. 14.
Mukherjee et al., "Studies of Single-Chain Antibody Expression in Quiescent *Escherichia coli*," Applied and Environmental Microbiology, May 2004, pp. 3005-3012, v. 70, n. 5.
Tian et al., "Genetic Screen Yields Mutations in Genes Encoding All Known Components of the *Escherichia coli* Signal Recognition Particle Pathway," Journal of Bacteriology, Jan. 2002, pp. 111-118, v. 184, n. 1.
Kujau et al., "Expression and secretion of functional miniantibodies McPC603scFvDhlx in cell-wall-less L-form strains of *Proteus mirabilis* and *Escherichia coli*: A comparison of the synthesis capacities of L-form strains with an *E. coli* producer strain," Appl. Microbiol. Biotechnol., 1998, pp. 51-58, v. 49.
Hoenger et al, "Direct in Situ Structural Analysis of Recombinant Outer Membrane Porins Expressed in an OmpA-Deficient Mutant *Escherichia coli* Strain," J. of Structural Biology, 1993, pp. 212-221, v. 111.
Hammarberg et al., "Characterization of an Extended Form of Recombinant Human Insulin-Like Growth Factor II," The J. of Biological Chemistry, Jun. 15, 1991, pp. 11058-11062, v. 266, n. 17.
European Search Report dated Jan. 29, 2008.
Ray et al., Production of salmon calcitonin by direct expression of a glycine-extended precursor in *Escherichia coli*, Protein Expression and Purification, 2002, 249-259, vol. 26.
Datsenko et al., One-step inactivation of chromosomal genes in *Escherichia coli* K-12 using PCR products, PNAS, 2000, 6640-6645, vol. 97, No. 12.
Wadensten et al., Purification and Characterization of Recombinant Human Insulin-like Growth Factor II (IGF-II) Expressed as a Secreted Fusion Protein in *Escherichia coli*, Biotechnology and Applied Biochemistry, 1991, 412-421. vol. 13.
Baneyx et al., Journal of Bacteriology, 1991, 2696-2703, vol. 173, No. 8.
Link et al., Journal of Bacteriology, 1997, 6228-6237, vol. 179, No. 20.
Nagahari et al., The EMBO Journal, 1985, 3589-3592, vol. 4, No. 13A.
Yang et al., Applied and Environmental Microbiology, 1998, 2869-2874, vol. 64, No. 8.
Patbase abstract corresponding to EP 0 338 410 B1, 1994.
English Abstract corresponding to JP 08074602 A.
Zakharova, M.V. et al., "Cloning and sequence analysis of the plasmid-borne genes encoding the Eco29kI restriction and modification enzymes," Gene 208 (1998), pp. 177-182.

(Continued)

*Primary Examiner*—Karen Cochrane Carlson
(74) *Attorney, Agent, or Firm*—Brooks Kushman P.C.

(57) ABSTRACT

A microorganism strain comprises a gene coding for a recombinant protein and a mutated gene coding for a host protein that is not a protease. The recombinant protein is secreted during a fermentation and the mutated gene coding for the host protein has been mutated so as to cause reduced expression of the host protein compared to the wild-type gene on which the mutated gene is based.

10 Claims, 4 Drawing Sheets

OTHER PUBLICATIONS

Majander, K. et al., "Extracellular secretion of polypeptides using a modified Escherichia coli flagellar secretion apparatus," Nature Biotechnology, v. 23, n. 4, Apr. 2005, pp. 475-481.

JP Literaturstelle Journal of Japan Society for Bioscience, Biotechnology and Agrochemistry, 1987, v. 61, n. 1, pp. 60-63.

JP Literaturstelle Journal of Japan Society for Bioscience, Biotechnology and Agrochemistry, 1988, v. 62, n. 3, pp. 504-505.

German Translation of Japanese Office Action dated Dec. 28, 2009, pp. 1-17.

Nagahari, K. et al., "Secretion into the culture medium of a foreign gene product from *Escherichia coli*: use of the ompF gene for secretion of human beta-endorphin," The EMBO Journal, v. 4, n. 13A, pp. 3589-3592, 1985.

Ray, M.V.L. et al., "Production of salmon calcitonin by direct expression of a glycine-extended precursor in *Escherichia coli*," Protein Expression and Purification, 26 (2002), pp. 249-259.

Machine Translation in English of JP Literaturstelle Journal of Japan Society for Bioscience, Biotechnology and Agrochemistry, 1987, v. 61, n. 1, pp. 60-63.

Machine Translation in English of JP Literaturstelle Journal of Japan Society for Bioscience, Biotechnology and Agrochemistry, 1988, v. 62, n. 3, pp. 504-505.

* cited by examiner

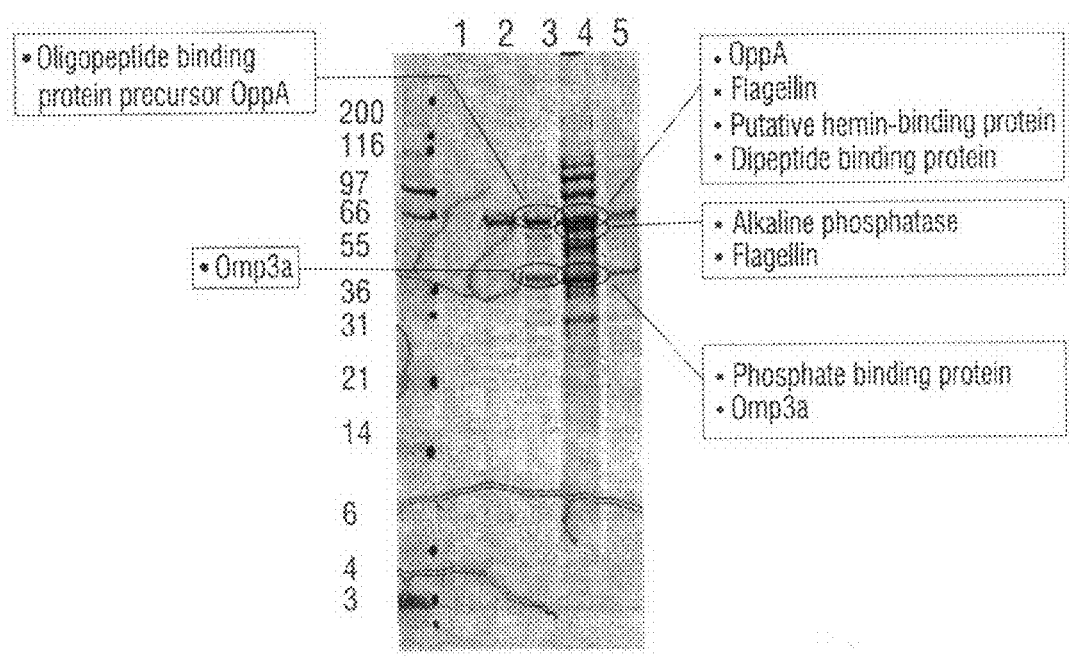
Fig. 1 Identification of contaminating proteins.
Lane 1: K802; 2: MM28; 3: WCM105; 4: BLR; 5: RV308

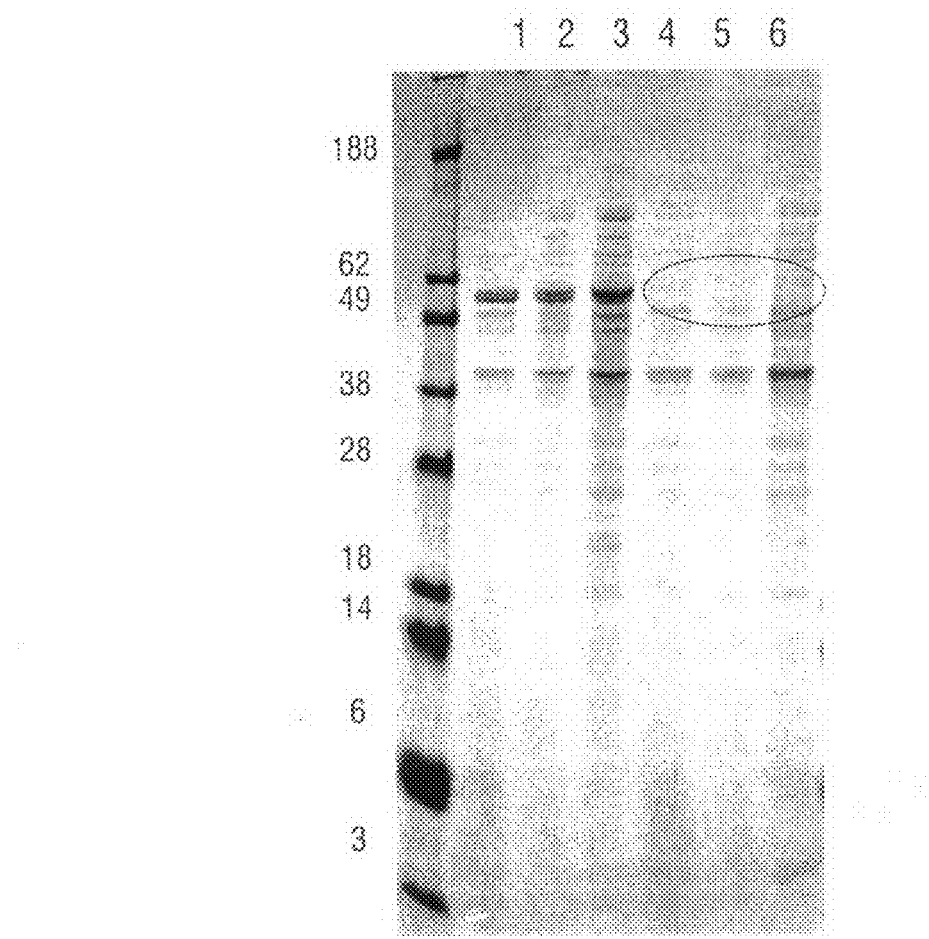
Fig. 2 Reduced production of contaminating proteins by a strain which may be employed for a process of the invention.
Lanes: 1, 2, 3: WCM105, 24, 48, 72 h;
4, 5, 6: WCM105ΔoppAΔyddSΔfliC, 24, 48, 72 h;

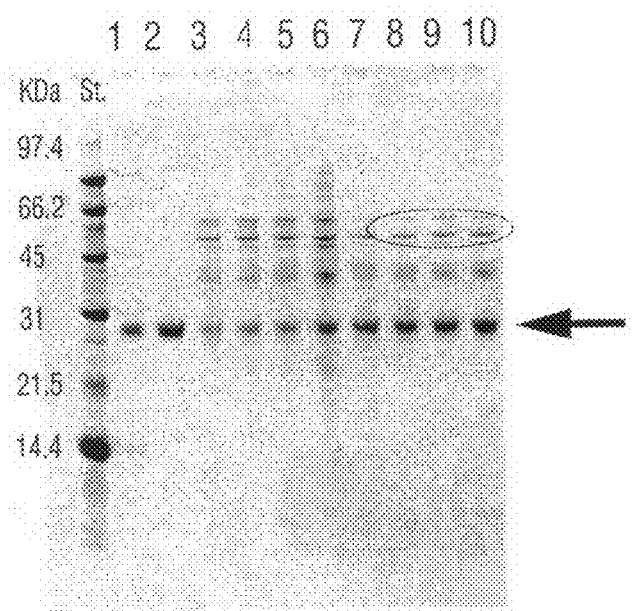
Fig. 3 Increased absolute and specific production of DsbG by a strain of the invention.
Lanes: 1, 2: DsbG (0.5 und 1 μg);
3, 4, 5, 6: WCM105 / pASK - dsbG, 9, 24, 48, 72 h;
7, 8, 9, 10: WCM105ΔoppAΔyddSΔfliC/pASK-dsbG, 9, 24, 48, 72 h.

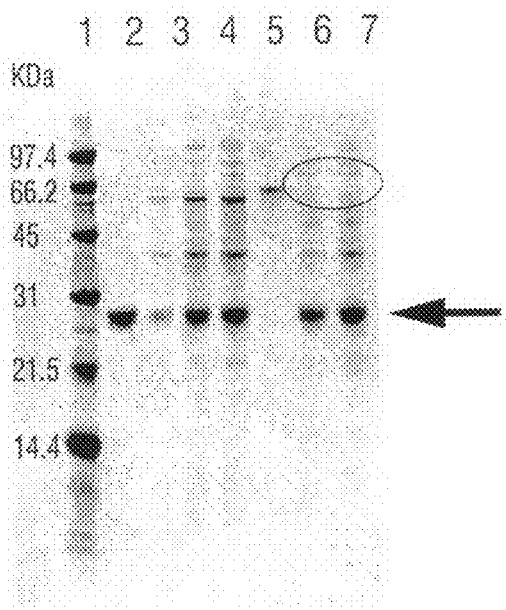
Fig. 4 Increased absolute and specific production of DsbG by a strain of the invention.
Lanes: 1: DsbG (0.5 μg);
2, 3, 4: K802 / pASK - dsbG, 24, 48, 72 h;
5, 6, 7: K802ΔoppAΔfliC/pASK-dsbG, 24, 48, 72 h.

SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: PCR-Primer pKD3fw

<400> SEQUENCE: 1
gtgtaggctg gagctgcttc                                                  20

<210> SEQ ID NO 2
<211> LENGTH: 19
<212> TYPE: DNA
<213> ORGANISM: Artificial Sequence
<220> FEATURE:
<223> OTHER INFORMATION: PCR-Primer pKD3rev

<400> SEQUENCE: 2
catatgaata tcctcctta                                                   19

<210> SEQ ID NO 3
<211> LENGTH: 75
<212> TYPE: DNA
<213> ORGANISM: Artificial Sequence
<220> FEATURE:
<223> OTHER INFORMATION: PCR-Primer ompA5

<400> SEQUENCE: 3
ccagtaccat gacactggtt tcatcaacaa caatggcccg acccatgaaa accaacatat      60
gaatatcctc cttag                                                       75

<210> SEQ ID NO 4
<211> LENGTH: 75
<212> TYPE: DNA
<213> ORGANISM: Artificial Sequence
<220> FEATURE:
<223> OTHER INFORMATION: PCR-Primer ompA6

<400> SEQUENCE: 4
gaccctggtt gtaagcgtca gaaccgatgc ggtcggtgta acccagaaca actacgtgta      60
ggctggagct gcttc                                                       75

<210> SEQ ID NO 5
<211> LENGTH: 20
<212> TYPE: DNA
<213> ORGANISM: Artificial Sequence
<220> FEATURE:
<223> OTHER INFORMATION: PCR-Primer ompA3

<400> SEQUENCE: 5
gacagctatc gcgattgcag                                                  20

<210> SEQ ID NO 6
<211> LENGTH: 20
<212> TYPE: DNA
<213> ORGANISM: Artificial Sequence
<220> FEATURE:
<223> OTHER INFORMATION: PCR-Primer ompA4

<400> SEQUENCE: 6
gctgagttac aacgtctttg                                                  20

<210> SEQ ID NO 7
<211> LENGTH: 75
<212> TYPE: DNA
<213> ORGANISM: Artificial Sequence
<220> FEATURE:
<223> OTHER INFORMATION: PCR-Primer oppA5

<400> SEQUENCE: 7
cactggcgga aaaacaaaca ctggtacgta acaatggttc agaagttcag tcattcatat    60
gaatatcctc cttag    75

<210> SEQ ID NO 8
<211> LENGTH: 75
<212> TYPE: DNA
<213> ORGANISM: Artificial Sequence
<220> FEATURE:
<223> OTHER INFORMATION: PCR-Primer oppA6

<400> SEQUENCE: 8
cattcacgta gtaataaaca ggaacaatgg ccgaatcctt atccagctgt tgttcgtgta    60
ggctggagct gcttc    75

<210> SEQ ID NO 9
<211> LENGTH: 20
<212> TYPE: DNA
<213> ORGANISM: Artificial Sequence
<220> FEATURE:
<223> OTHER INFORMATION: PCR-Primer oppA3

<400> SEQUENCE: 9
gcggatcttt gccggtatag    20

<210> SEQ ID NO 10
<211> LENGTH: 20
<212> TYPE: DNA
<213> ORGANISM: Artificial Sequence
<220> FEATURE:
<223> OTHER INFORMATION: PCR-Primer oppA4

<400> SEQUENCE: 10
gaccaacatc accaagagaa    20

<210> SEQ ID NO 11
<211> LENGTH: 70
<212> TYPE: DNA
<213> ORGANISM: Artificial Sequence
<220> FEATURE:
<223> OTHER INFORMATION: PCR-Primer dppA1

<400> SEQUENCE: 11
aagggtttaa cccgcagctg tttacctccg gcaccaccta tgacgcctct catatgaata    60
tcctccttag    70

<210> SEQ ID NO 12
<211> LENGTH: 70
<212> TYPE: DNA
<213> ORGANISM: Artificial Sequence
<220> FEATURE:
<223> OTHER INFORMATION: PCR-Primer dppA2

<400> SEQUENCE: 12
tgccggagcc tgatcgtgca tcaccacctg cgcttgtttg tacagttcaa gtgtaggctg    60

-continued

```
gagctgcttc                                                            70

<210> SEQ ID NO 13
<211> LENGTH: 20
<212> TYPE: DNA
<213> ORGANISM: Artificial Sequence
<220> FEATURE:
<223> OTHER INFORMATION: PCR-Primer dppA3

<400> SEQUENCE: 13 gtcaggatg ctgaagcttg                                                  20

<210> SEQ ID NO 14
<211> LENGTH: 20
<212> TYPE: DNA
<213> ORGANISM: Artificial Sequence
<220> FEATURE:
<223> OTHER INFORMATION: PCR-Primer dppA4

<400> SEQUENCE: 14
tgtttgccta atggatcaac                                                 20

<210> SEQ ID NO 15
<211> LENGTH: 70
<212> TYPE: DNA
<213> ORGANISM: Artificial Sequence
<220> FEATURE:
<223> OTHER INFORMATION: PCR-Primer fliC1

<400> SEQUENCE: 15
tgcgtattaa cagcgcgaag gatgacgcag cgggtcaggc gattgctaac catatgaata    60
tcctccttag                                                            70

<210> SEQ ID NO 16
<211> LENGTH: 70
<212> TYPE: DNA
<213> ORGANISM: Artificial Sequence
<220> FEATURE:
<223> OTHER INFORMATION: PCR-Primer fliC2

<400> SEQUENCE: 16
ggagttaccg gcctgctgga tgatctgcgc tttcgacata ttggacactt gtgtaggctg    60
gagctgcttc                                                            70

<210> SEQ ID NO 17
<211> LENGTH: 21
<212> TYPE: DNA
<213> ORGANISM: Artificial Sequence
<220> FEATURE:
<223> OTHER INFORMATION: PCR-Primer fliC3

<400> SEQUENCE: 17
tatcaacaag aaccagtctg c                                               21

<210> SEQ ID NO 18
<211> LENGTH: 20
<212> TYPE: DNA
<213> ORGANISM: Artificial Sequence
<220> FEATURE:
<223> OTHER INFORMATION: PCR-Primer fliC4

<400> SEQUENCE: 18
agacagaacc tgctgcggta                                                 20
```

<210> SEQ ID NO 19
<211> LENGTH: 70
<212> TYPE: DNA
<213> ORGANISM: Artificial Sequence
<220> FEATURE:
<223> OTHER INFORMATION: PCR-Primer yddS1

<400> SEQUENCE: 19
attggtaagg ccgccgatcc acaaaccctc gacccggcgg taacaataga catatgaata    60
tcctccttag    70

<210> SEQ ID NO 20
<211> LENGTH: 70
<212> TYPE: DNA
<213> ORGANISM: Artificial Sequence
<220> FEATURE:
<223> OTHER INFORMATION: PCR-Primer yddS2

<400> SEQUENCE: 20
acaggtacac ataagcagcg tcatcaatga cgattttctg tgcctgctgg gtgtaggctg    60
gagctgcttc    70

<210> SEQ ID NO 21
<211> LENGTH: 20
<212> TYPE: DNA
<213> ORGANISM: Artificial Sequence
<220> FEATURE:
<223> OTHER INFORMATION: PCR-Primer yddS3

<400> SEQUENCE: 21
attgctcgcg ctcgtccttg    20

<210> SEQ ID NO 22
<211> LENGTH: 20
<212> TYPE: DNA
<213> ORGANISM: Artificial Sequence
<220> FEATURE:
<223> OTHER INFORMATION: PCR-Primer yddS4

<400> SEQUENCE: 22
cctgttccag catgggattg    20

<210> SEQ ID NO 23
<211> LENGTH: 41
<212> TYPE: DNA
<213> ORGANISM: Artificial Sequence
<220> FEATURE:
<223> OTHER INFORMATION: PCR-Primer dsbGfw

<400> SEQUENCE: 23
gctctagagg atccgaaaag gacaaattaa tgttaaaaaa g    41

<210> SEQ ID NO 24
<211> LENGTH: 34
<212> TYPE: DNA
<213> ORGANISM: Artificial Sequence
<220> FEATURE:
<223> OTHER INFORMATION: PCR-Primer dsbGrev

<400> SEQUENCE: 24
cgaattctta tttattcccc ataatgatat taag    34

MICROORGANISM STRAIN FOR PRODUCING RECOMBINANT PROTEINS

BACKGROUND OF THE INVENTION

1. Field of the Invention

The present invention relates to microorganism strains capable of improving the production of recombinant proteins. The present invention also relates to processes for preparing such strains and to processes for producing recombinant proteins by employing the strains.

2. Background Art

The large-scale economic production of recombinant proteins is becoming increasingly important to the biotechnological and pharmaceutical industries. Generally, recombinant proteins are prepared either in mammalian cell cultures or in microbial systems. Microbial systems have the advantage over mammalian cell cultures in that it is possible to produce in this way recombinant proteins within a shorter period of time and at lower costs. The most common microbial organism for producing recombinant proteins is the bacterium E. coli. E. coli can in principle produce proteins in various ways:

1. intracellular production in the form of soluble protein;
2. intracellular production in the form of inclusion bodies;
3. secretion into the periplasm or the surrounding nutrient medium.

The complexity and costs of preparing the desired protein are also substantially determined by the costs of purifying the crude product to give said desired protein. These costs are in addition to the costs of producing the crude product which is present after fermentation in the form of a mixture comprising the recombinant protein and host proteins secreted naturally by the cell. The purification includes in most cases several stages and is carried out by means of chromatographic processes. In this connection, the removal of contaminating host proteins, some of which are immunogenic or toxic, plays an important part.

In E. coli, proteins are typically secreted via the "sec pathway". To this end, the gene of the protein to be produced is linked to a signal sequence, resulting in a signal peptide-protein fusion being produced. The signal peptide mediates secretion of the protein through the cytoplasmic membrane into the periplasm via the endogenous bacterial sec system. In the process, the signal sequence is removed and the desired protein is obtained in the periplasm. The protein may then be purified from the periplasm. Under certain conditions or in certain bacterial strains, the protein is released from the periplasm into the surrounding nutrient medium (e.g. Ray et al. 2002; EP0338410B1; Nagahari et al. 1985; Yang et al., 1998) and may be purified from the latter.

Compared to other preparation processes, secretion offers the advantage of obtaining native, soluble, correctly folded protein which, when compared to the inclusion body process, need not be denatured and renatured—a step accompanied by high losses of yield. Moreover, the product obtained is contaminated with fewer host proteins compared to intracellular, soluble production, since the bacterial periplasm contains substantially fewer host proteins than the cytoplasm.

Secretion of the proteins into the surrounding nutrient medium offers the additional advantage of the protein in this case being present in an even purer form as compared to secretion into the periplasm. Moreover, the first purification step does not require any complicated preparation of the periplasm but rather requires a much simpler and more reproducible removal of whole cells.

The crude product in the preparation of proteins by secretion is contaminated with fewer host proteins over all than in intracellular production. Nevertheless, contaminating host proteins also play a part here, especially host proteins which are also naturally secreted by the bacterium and then located in the periplasm or in the outer membrane. These proteins are distinguished by the fact that their genes naturally include a signal sequence that mediates the secretion. Apart from the fact that these host proteins contaminate the crude product, they also compete with the protein to be produced for the components of the secretion apparatus, possibly resulting in a reduced secretion of the protein to be produced. However, the host proteins which cause contamination of the crude product fulfill a physiological role in the host cell. For example, these proteins may be involved in chemotaxis and special transport processes.

The literature describes that the production of proteolysis-sensitive, secreted proteins can be improved by deleting genes coding for periplasmic proteases. This has been described for degP, ompT, ptr, (U.S. Pat. No. 5,264,365; Baneyx & Georgiou, 1991; Wadensten et al., 1991). This effect can be attributed to eliminating the activity of the proteases which degrade the produced protein in the starting cell. Proteases endogenous to the host frequently degrade especially heterologously produced proteins in cells. However, the amount of contaminating proteases is negligible, since they are produced only in very low amounts in the host cell, due to their high activity and enzymic function. Thus, deleting these genes does not affect the degree of purity of the produced proteins.

WO 2004/035792 A1 describes the modification of certain host proteins, (e.g. PhoS/PstS, DppA, MBP, Trx) by mutations in individual amino acids, which alter the physical or biochemical properties (isoelectric point, hydrophobicity, size). This alteration of the physical or biochemical properties results in the resulting modified contaminating host proteins no longer being copurified with the desired produced protein in each case, since they behave differently on a chromatographic column, for example. The method cannot be utilized for producing any protein, since the contaminating host proteins have to be altered specifically for each protein to be produced because each protein has different biochemical properties. In the process according to WO 2004/035792 A1, production and functionality of the contaminating host proteins are retained despite their modification. Thus, the degree of purity of the crude product of the produced protein does not change but in each case removal of the contaminating host proteins from the protein is facilitated.

WO 98/18946 describes cells which, in addition to the protein to be produced, coexpress Dsb proteins and have a deletion in the wild-type pstS gene but at the same time express a pstS variant. Here too, the amount of contaminating host protein is thus unchanged.

SUMMARY OF THE INVENTION

It is an object of the present invention to provide microorganism strains facilitating production of recombinant proteins.

BRIEF DESCRIPTION OF THE DRAWINGS

FIG. 1 depicts the supernatants of 48 h cultures in LB, fractionated on a 12% NuPAGE gel (Invitrogen), and identified proteins of example 1.

FIG. 2 depicts the supernatants of cultures in LB+1% Glc, fractionated on a 12% NuPAGE gel and stained with Coomassie, of examples 3 and 5.

FIG. 3 depicts the supernatants of cultures in LB+1% Glc, fractionated on a 12% NUPAGE gel and stained with Coomassie. In each case 1 μl of each supernatant is loaded. The arrow indicates the produced DsbG (26 kDa), with the ellipse indicating the deleted proteins.

FIG. 4 depicts the supernatants of cultures in LB+1% Glc, fractionated on a 12% NuPAGE gel and stained with Coomassie. In each case 10 μl of each supernatant is loaded. The arrow indicates the produced DsbG (26 kDa), with the ellipse indicating the deleted proteins.

DETAILED DESCRIPTION OF THE PREFERRED EMBODIMENT(S)

In an embodiment of the present invention, a microorganism strain comprises a gene coding for a recombinant protein and a mutated gene coding for a host protein that is not a protease. The recombinant protein is secreted during fermentation and the mutated gene coding for the host protein has been mutated so as to cause reduced expression of the host protein compared to the wild-type gene on which the mutated gene is based.

Advantageously, for economic production of a protein, the produced recombinant protein is contaminated with a very low amount of as few host proteins as possible even in the crude product, i.e. directly after fermentation, when it is present in a mixture comprising the recombinant protein and contaminating host proteins. As a result, the specific yield of recombinant protein is increased, thereby simplifying subsequent purification of the recombinant protein. This advantage is offered by the bacterial strains of the invention.

For purposes of the present invention, reduced expression means preferably that the amount of the protein in question produced and secreted is reduced by 25 to 100% compared to a wild-type cell. More preferably, the amount of the protein in question produced and secreted is reduced by 75 to 100% compared to a wild-type cell. Most preferably, the production and secretion of the protein in question is completely switched off. The host protein is preferably selected from the group consisting of OppA, OmpA, DppA, YddS, FliC, PhoA, and PhoS.

Preferably, the recombinant protein is secreted into the periplasm or into the fermentation medium during fermentation. More preferably, the recombinant protein is secreted into the fermentation medium.

Preferably, the recombinant protein is a heterologous protein. The microorganism strain is preferably a bacterial strain. More preferably, the microorganism strain is a bacterial strain of the Enterobacteriaceae family. Most preferably, the microorganism strain is a strain of the species *Escherichia coli*. Particular preference is given to an *Escherichia (E.) coli* strain which is distinguished by having after fermentation a higher concentration of the recombinant protein in the periplasm, or more preferably in the surrounding nutrient medium, than the strain *E. coli* W3110 (ATCC 27325). Strains of this kind are referred to as secretion strains hereinbelow.

Preferably, the secretion strains are strains which after fermentation have more than 50 mg/l of the recombinant protein in the surrounding nutrient medium. More preferably, the secretion strains are strains which after fermentation have more than 100 mg/l of the recombinant protein in the surrounding nutrient medium. Most preferably, the secretion strains are strains which after fermentation have more than 200 mg/l of the recombinant protein in the surrounding nutrient medium.

Additional features of a strain of the invention are mentioned in the context of its preparation. Accordingly, the features mentioned below of the starting strains analogously also apply to a strain of the invention.

A microorganism strain of the invention is obtained by a process which comprises employing a host cell transformed with a gene coding for a recombinant protein in a fermentation for producing the recombinant protein. The host cell secretes the recombinant protein and other host proteins into the fermentation medium, thus producing a crude product containing the recombinant protein and other host proteins, characterizing the other host proteins and reducing or preventing expression of a gene coding for any of these host proteins. Preferably, the gene coding for a recombinant protein is removed from the microorganism strain during the process in order to reduce or prevent expression of the host proteins.

The host cells are cells of a microorganism strain, for example, a yeast or bacterial strain. The bacterial strain is preferably a strain of the Enterobacteriaceae family. More preferably, the bacterial strain is a strain of the species *Escherichia coli*. Most preferably, the bacterial strain is an *Escherichia (E.) coli* strain which is distinguished by having after fermentation a higher concentration of the recombinant protein in the periplasm, or more preferably in the surrounding nutrient medium, than the strain *E. coli* W3110 (ATCC 27325).

The secretion strains are preferably strains which after fermentation have more than 10 mg/l of the recombinant protein in the surrounding nutrient medium. More preferably, the secretion strains are strains which after fermentation have more than 50 mg/l of the recombinant protein in the surrounding nutrient medium. Most preferably, the secretion strains are strains which after fermentation have more than 100 mg/l of the recombinant protein in the surrounding nutrient medium.

Particularly useful strains include the following *E. coli* strains:

BLR: Ray et al. 2002, commercially available from Novagen
K802=CGSC* 5610: Yang et al., 1998
WCM105: preparable according to EP0338410B1
MM28=CGSC* #5892: Nagahari et al. 1985
RV308=ATCC** 31608; EP0677109B1
RR1: ATCC** 31434: Nagahari et al., 1985
KG1005 ompT: Wadensten et al., 1991
* commercially available via the *E. coli* Genetic Stock Center CGSC (830 Kline Biology Tower, MCD Biology Department, 266 Whitney Ave., PO box 208103, Yale University, New Haven),
** commercially available from LGC Promochem, Mercatorstr. 51, 46485 Wesel, Germany The secreted protein is a recombinant protein which is produced and secreted by the host cell. Secretion of the protein is preferably made possible by fusion of its gene to a signal sequence. The produced protein is preferably a protein used in industrial approaches or a protein employed as a pharmaceutical drug (biologics, biopharmaceuticals).

Host proteins contaminating the produced protein are identified by methods known to the skilled worker. Such methods include, for example, fractionating the cell-free supernatant after culturing in an SDS-polyacrylamide gel and subsequent analysis of the individual bands by N-terminal sequencing or peptide fingerprinting.

Examples of proteins contaminating the secreted product in *E. coli* are: OppA, DppA, OmpA, YddS, FliC, PhoA, PhoS, moreover any combination of these proteins.

Oligopeptide binding protein OppA: Swiss Prot #P23843
61 kDa, one of the major proteins in the periplasm, component of oligopeptide permease (binding protein-dependent transport system), binds peptides of up to 5 AA with high affinity, is bound by SecB, also possesses chaperone function, is involved in the uptake of aminoglycoside antibiotics.

Dipeptide binding protein DppA: Swiss Prot # P23847
61 kDa, periplasmic, dipeptide binding protein of a transport system, required for peptide chemotaxis, chaperone-like function (in Rhodobacter).

Outer membrane protein Omp3a=OmpA: NCBI # NP_286832
37 kDa, located in outer membrane, required for, the action of colicins K and L, stabilization during conjugation, receptor for phages, porin with low permeability for small solutes.

Flagellin FliC: Swiss Prot # P04949, 51 kDa, flagella subunit putatives hemin binding protein YddS: Swiss Prot #Q8XAU4 57 kDa, putative dipeptide transport protein.

Alkaline phosphatase PhoA: E.C.3.1.3.1, 49 kDa, periplasmic protein catalyzing orthophosphate monoester cleavage.

Phosphate binding protein PhoS: 37 kDa, periplasmic protein; component of the PTS phosphate uptake system. Both alkaline phosphatase, PhoA, and phosphate binding protein, PhoS, are involved in supplying *E. coli* with phosphate.

Subsequently, expression of the genes of these proteins in the host cells is reduced or prevented. Since the proteins naturally fulfill a physiological role in the bacteria, it is surprising that the drastically reduced formation of these proteins is compatible with a survival of the cells and an effective metabolism required for overproduction of proteins.

Methods for reducing or preventing expression of genes so that the special host proteins encoded by the gene in the starting cell are no longer produced or produced to a lesser extent are known.

Expression of any of the genes may be reduced or prevented, for example, by any of the following measures:
attenuation of the promoter corresponding to the gene by means of suitable base substitutions
inactivation/modification of a transcriptional activator required for expression
attenuation of translational start signals (e.g. ribosomal binding site, start codon) by means of suitable base substitutions
removal of mRNA-stabilizing regions of the gene
overexpression of DNA regions coding for specific anti-sense RNA
deletion of the entire gene or at least part thereof
destruction of the gene by inserting, for example, an antibiotic resistance cassette
introduction of reading frame shifts into the corresponding gene due to nucleotide deletions or nucleotide insertions Methods of replacing any chromosomal DNA sequence with a sequence which, although homologous, has been modified by base insertions, base deletions or base substitutions are known to the skilled worker. Thus, it is possible, for example, to use in *Escherichia coli* the system described by Link et al. (1997), in order to replace the chromosomal wild-type sequence of the gene of a contaminating protein with a mutated allele by means of integrative plasmids via the mechanism of homologous recombination. Preferably, in such methods, a deletion is introduced into a gene of a contaminating host protein. This may be achieved by cloning the gene first into a plasmid vector (e.g. pUC18, pBR322, pACYC184), after amplification by means of PCR using specific primers covering the complete gene. Internal regions of the gene may be removed by restriction of the plasmid obtained in this way with suitable restriction endonucleases which cut only within the region of the gene. In this way it is possible, after religation of the restricted plasmid, to introduce an internal deletion into the gene. As an alternative to religation of the plasmid restricted in the gene it is also possible to clone an antibiotic resistance cassette into the gene. For example, a gene may be deleted with the aid of the λ-Red recombinase system by Datsenko and Wanner (2000, PNAS, 97 (12), pp. 6640-6645).

Another embodiment of the present invention, relates to a process for fermentative production of a recombinant protein by means of a bacterial strain harboring a recombinant gene coding for the recombinant protein in a fermentation medium. The process of this embodiment comprises culturing a microorganism strain of the invention in the fermentation medium and, after fermentation, separating the fermentation medium from the cells of the bacterial strain.

Preferably, the recombinant protein is purified from the fermentation medium, after the latter has been removed. The process of the invention simplifies purification of the recombinant protein produced from the fermentation medium.

The gene coding for the protein to be produced is preferably provided with expression signals functional in this host organism (promoter, transcription and translation start sites, ribosomal binding site). Furthermore, the gene coding for the protein to be produced is linked to a signal sequence which results in the protein to be produced being produced initially as a fusion with the signal peptide encoded by the signal sequence. The signal peptide causes the produced protein to be secreted. Examples of useful signal sequences include phoA, ompA, pelB, ompF, ompT, lamB, malE, staphylococcal protein A, stII.

The produced protein is secreted, for example, via the sec apparatus of the cell. After secretion into the periplasm, a signal peptidase (e.g. LepB in *E. coli*) removes the signal peptide, resulting in the desired protein.

The gene of the protein to be produced including expression and secretion signals is introduced into the host cell. This is carried out using a vector (for example, a plasmid such as a derivative of a known expression vector such as pUC18, pBR322, pACYC184, pASK-IBA3 or pET). The gene may also be expressed from the chromosome of the host cell.

Fermentation of the bacterial strain for protein production according to the invention is preferably carried out in a complete medium or minimal salt medium. These media are known from the literature. In principle, any utilizable sugars, sugar alcohols, organic acids or their salts, starch hydrolysates, molasses or other substances may be used as the carbon source. Preferably, the carbon source includes glucose or glycerol. It is also possible to provide a combined feed consisting of several different carbon sources. Nitrogen sources which may be used are urea, ammonia and its salts, nitrate salts and other nitrogen sources. Possible nitrogen sources also include complex amino acid mixtures such as yeast extract, peptone, malt extract, soya peptone, casamino acids, corn steep liquor and NZ amines (e.g. Kerry Bio-Science, Chicago, USA). Additional components such as vitamins, salts, yeast extract, amino acids and trace elements, which improve cell growth are optionally added to the medium.

Preferably, the strain is incubated under aerobic culturing conditions over a period of from 16-150 h and within the range of the optimal growth temperature for the particular strain. A preferred optimal temperature range is from 15-55° C. More preferably, the temperature range is between 30 and 37° C.

In a variation of the present invention, the strain may be grown in shaker flasks or in a fermenter without any volume restrictions. Culturing may be carried out by way of a batch process, a fed batch process or a continuous process.

In a variation of the present invention, proteins may be purified from the periplasm or the culture medium by processes known to the skilled worker, such as centrifugation of the medium to remove the cells and subsequent chromatographic purification, complexing, filtration or precipitation of the protein.

The invention is further illustrated by the following examples.

Example 1

Identification of Contaminating Host Proteins

The following *E. coli* secretion strains which are known from the literature, generally accessible and commercially available are cultured in Luria-Bertani medium ("LB medium") in 100 ml Erlenmeyer flasks at 30° C. for 48 h:
 BLR: Ray et al. 2002, available via Novagen
 K802=CGSC* #5610: Yang et al., 1998
 WCM105: preparable according to EP0338410B1
 MM28=CGSC* #5892: Nagahari et al. 1985
 RV308=ATCC** 31608; EP0677109B1
 RR1: ATCC** 31434: Nagahari et al., 1985
 KG1005 ompT: Wadensten et al., 1991
* available via the *E. coli* Genetic Stock Center CGSC (830 Kline Biology Tower, MCD Biology Department, 266 Whitney Ave., PO box 208103, Yale University, New Haven, Conn. 06520-8193),
** available via: LGC Promochem, Mercatorstr. 51, 46485 Wesel, Germany The cells are subsequently removed by centrifugation at 13 000 g for 10 min. In each case 30 µl of supernatant (medium) are admixed with SDS sample buffer (5×SDS sample buffer: 125 mM Tris pH 6.8; 10% glycerol; 0.5% SDS; 0.05% bromophenol blue; 5% β-mercaptoethanol) and fractionated in a 12% NuPAGE® Bis-Tris Gel (Invitrogen Cat. No. NP0341) with 1× MES-containing Running Buffer (20× MES—Running Buffer, Invitrogen Cat. No. NP0002) (electrophoretic parameters: 40 min at 200 V). The gel is then stained with Coomassie Blue staining solution (dissolve 1 tablet of PlusOne Coomassie tablets, Phast Gel Blue R-350 (Amersham 17-0518-01) in 80 ml of $H_2O$, +120 ml of methanol, +200 ml of 20% acetic acid) for 1 hour and destained in destaining solution (300 ml of methanol, 100 ml of glacial acetic acid, 600 ml of fully demineralized $H_2O$). After washing in fully demineralized water, prominent bands are identified on the gel (see FIG. 1). They are caused by proteins contaminating the crude product. The corresponding bands are excised and alternately washed with acetonitrile and 50% ammonium bicarbonate buffer (pH 8.5). If required, the disulfide bridges are reduced with DTT and iodoacetamide. After proteolysis with trypsin, the resulting peptides are measured by means of MALDI-TOF mass spectrometry. The proteins studied are identified by comparison with theoretically calculated masses (expected peptides) and database entries.

Seven conspicuous proteins are identified:
 Oligopeptide binding protein OppA: Swiss Prot # P23843
 Dipeptide binding protein DppA: Swiss Prot # P23847
 Outer membrane protein Onp3a=OmpA: NCBI # NP_286832
 Flagellin FliC: Swiss Prot # P04949
 putatives Hemin binding protein YddS: Swiss Prot # Q8XAU4
 Alkaline phosphatase PhoA: E.C.3.1.3.1 Swiss Prot # P00634
 Phosphate binding protein PhoS Swiss prot Swiss Prot # P06128

Example 2

Deletion of Genes of Contaminating Host Proteins

A large internal region of the respective genes in the respective strains is deleted using the λ-Red recombinase system by Datsenko and Wanner (2000, PNAS, 97 (12), pp. 6640-6645). For this purpose, the gene region to be removed is first replaced with a chloramphenicol resistance cassette which is then eliminated again by using yeast FLP recombinase and special "FRT" flanks on the cassette.

The deletion is carried out as follows:

PCR:
 Template:
 The template used is pKD3 (chloramphenicol resistance; available via the *E. coli* Genetic Stock Center CGSC as CGSC #7631).
 Oligos:
 Forward Oligo: 36-50 bp of homologous sequence from the start of the gene to be removed +20 bp of homologous plasmid sequence:

(SEQ. ID NO 1)
5'- 36-50 bp chrom. -GTG TAG GCT GGA GCT GCT TC -3'

Reverse Oligo: 36-50 bp of homologous sequence from the end of the gene to be removed +20 bp of plasmid sequence (counterstrand):

(SEQ. ID NO 2)
5'- 36-50 chrom. - CAT ATG AAT ATC CTC CTT AG -3'

Polymerase:
 Pfu or Taq
 Length of product:
 pKD3: 1.1 kb

Purification of the PCR Product:
 The PCR product is purified (e.g. via Qiapräp columns) and digested with DpnI (2 h at 37° C. in corresponding buffer), and then purified again and eluted in 30 µl of distilled water (=PCR prep).

Preparation of Electrocompetent Cells:
 pKD46=λ Red recombinase expression plasmid (arabinose-inducible), available via the *E. coli* Genetic Stock Center CGSC as CGSC #7739, Amp resistance, temperature-sensitive origin: all steps at 30° C. max.
 Transformation of the plasmid into the target strain to be modified (expression/incubation at 30° C.)
 Prepare competent cells from target strain+plasmid for electroporation.
 Medium for growing the cells: SOB medium:

| 20 g/l | tryptone |
|---|---|
| 5 g/l | yeast extract |
| 0.5 g/l | NaCl |
| 2.5 g/l | KCl |
| 10 mM | MgCl |
| +0.2% | arabinose |
| +100 mg/l | ampicillin |

Preparation of Electroporation-Competent Cells:
culturing at 30° C.
harvesting of cells at $OD_{600}$~0.6
concentrate approx. 100-fold and wash 3× with ice-cold glycerol (10%)

Recombination:
10 μl of PCR prep (approx. 10-100 ng of purified PCR DNA) are transformed into the electrocompetent cells
Phenotypic expression: take up transformation mixture in 1 ml of LB and incubate at 37° C. for 1 h) and select on LBcam plates. Incubation at 37° C.

Curing of pKD46 (CGSC #7739):
A clone obtained in this way and containing a resistance cassette is streaked out on 2 LB plates and incubated in parallel at 37° C. and 43° C.
Individual colonies from these plates are streaked out on LB amp (LB with 100 mg/l ampicillin) and LB and incubated at 30° C.
Approx. 8 clones thereof are purified on LB cam (LB with 30 mg/l) (37° C.).

PCR Check of Clones:
Suitable oligos (see below and Datsenko and Wanner, 2000) are used to check, whether the resistance cassette is actually located at the site of the gene to be removed in the chromosome.

Removal of the Chromosomal Antibiotic Resistance Cassette:
PCP20 (available via the *E. coli* Genetic Stock Center CGSC as CGSC #7629)="FLP" recombinase expression plasmid, Amp resistance, temperature-sensitive origin: all steps at 30° C. max.
An amp-sensitive clone (cam-resistant from curing) is transformed with pCP20, selection on LB amp at 30° C.
8 transformants are purified on LB, incubation at 37° C.,
Individual colonies are again streaked out on LB and incubated at 43° C.
Of these, approx. 12 clones are tested for cam and amp sensitivity.
amp/cam-sensitive clones have lost the resistance cassette and pPC20.
⇒Deletion clone without integrated Cam cassette.

Specifically, the following oligos are used for constructing the individual deletion mutants and the following PCR products are obtained:

Deletion of OmpA

Primer for PCR:

OmpA5:

```
                                          (SEQ ID NO. 3)
CCAGTACCAT GACACTGGTT TCATCAACAA CAATGGCCCG

ACCCATGAAA ACCAA CAT ATG AAT ATC CTC CTT AG
```

OmpA6:

```
                                          (SEQ ID NO. 4)
GACCCTGGTT GTAAGCGTCA GAACCGATGC GGTCGGTGTA

ACCCAGAACA ACTAC GTG TAG GCT GGA GCT GCT TC
```

→ PCR with PKD3 (available via the *E. coli* Genetic Stock Center CGSC as CGSC #7631): Product: 1114 bp; 598 bp of ompA are replaced with 1014 bp of Cam resistance upon recombination Checking of integration/deletion with primers:

```
OmpA3:   GACAGCTATCGCGATTGCAG     (SEQ ID NO. 5)
OmpA4:   GCTGAGTTACAACGTCTTTG     (SEQ ID NO. 6)
```

Products: WT: 1022 bp; insertion mutant: 1486 bp; deletion mutant: approx. 430 bp
As described, the following strains are prepared:
BLRΔompA
K802ΔompA
WCM105ΔompA
MM28ΔompA
RV308ΔompA
RR1ΔompA
KG1005ompTΔompA Deletion of OppA Primer for PCR:

OppA5:

```
                                          (SEQ ID NO. 7)
CACTGGCGGA AAAACAAACA CTGGTACGTA ACAATGGTTC

AGAAGTTCAG TCATT CAT ATG AAT ATC CTC CTT AG
```

OppA6:

```
                                          (SEQ ID NO. 8)
CATTCACGTA GTAATAAACA GGAACAATGG CCGAATCCTT

ATCCAGCTGT TGTTC GTG TAG GCT GGA GCT GCT TC
```

→ PCR with pKD3: Product: 1114 bp; 1331 bp of oppA are replaced with 1014 bp of Cam resistance upon recombination Checking of integration/deletion with primers:

```
OppA3:   GCG GAT CTT TGC CGG TAT AG (SEQ ID NO. 9)
OppA4:   GAC CAA CAT CAC CAA GAG AA (SEQ ID NO. 10)
```

Products: WT: 1587 bp; insertion mutant: 1270 bp; deletion mutant: approx. 260 bp
The following strains are produced:
BLRΔoppA
K802ΔoppA
WCM105ΔoppA
MM28ΔoppA
RV308ΔoppA
RR1ΔoppA
KG1005ompTΔoppA Deletion of DppA Primer for PCR:

DppA1:

```
                                          (SEQ ID NO. 11)
AAGGGTTTAACCCGCAGCTGTTTACCTCCGGCACCACCTATGACGCCTCT

CAT ATG AAT ATC CTC CTT AG
```

DppA2:

(SEQ ID NO. 12)

TGCCGGAGCCTGATCGTGCATCACCACCTGCGCTTGTTTGTACAGTTCAA GTG TAG GCT GGA GCT GCT TC

→ with pKD3: Product: 1114 bp; 1381 bp of dppA are replaced with 1014 bp of Cam resistance upon recombination
  Checking of integration/deletion with primers:

DppA3:   GTCAGGGATGCTGAAGCTTG   (SEQ ID NO. 13)

DppA4:   TGTTTGCCTAATGGATCAAC   (SEQ ID NO. 14)

Products: WT: 1587 bp; insertion mutant: 1193 bp; deletion mutant: approx. 566 bp
  The following strains are produced:
  BLRΔdppA
  K802ΔdppA
  WCM105ΔdppA
  MM28ΔdppA
  RV308ΔdppA
  RR1ΔdppA
  KG1005ompTΔdppA Deletion of FliC Primer for PCR:

FliC1:

(SEQ ID NO. 15)

TGCGTATTAACAGCGCGAAGGATGACGCAGCGGGTCAGGCGATTGCTAAC CAT ATG AAT ATC CTC CTT AG

FliC2:

(SEQ ID NO. 16)

GGAGTTACCGGCCTGCTGGATGATCTGCGCTTTCGACATATTGGACACTT GTG TAG GCT GGA GCT GCT TC

→ PCR with pKD3: Product: 1114 bp; 1334 bp of fliC are replaced with 1014 bp of Cam resistance upon recombination
  Checking of integration/deletion with primers:

FliC3:   TATCAACAAGAACCAGTCTGC   (SEQ ID NO. 17)

FliC4:   AGACAGAACCTGCTGCGGTA    (SEQ ID NO. 18)

Products: WT: 1432 bp; insertion mutant: 1112 bp; deletion mutant: approx. 110 bp
  The following strains are produced:
  BLRΔfliC
  K802ΔfliC
  WCM105ΔfliC
  MM28ΔfliC
  RV308ΔfliC
  RR1ΔfliC
  KG1005ompTΔfliC Deletion of YddS Primer for PCR:

YddS1:

(SEQ ID NO. 19)

ATTGGTAAGGCCGCCGATCCACAAACCCTCGACCCGGCGGTAACAATAGA CAT ATG AAT ATC CTC CTT AG

YddS2:

(SEQ ID NO. 20)

ACAGGTACACATAAGCAGCGTCATCAATGACGATTTTCTGTGCCTGCTGG GTG TAG GCT GGA GCT GCT TC

→ PCR with pKD3: Product: 1114 bp; 1350 bp of fliC are replaced with 1014 bp of Cam resistance upon recombination
  Checking of integration/deletion with primers:

YddS3:   ATTGCTCGCGCTCGTCCTTG   (SEQ ID NO. 21)

YddS4:   CCTGTTCCAGCATGGGATTG   (SEQ ID NO. 22)

Products: WT: 1432 bp; insertion mutant: 1156 bp; deletion mutant: approx. 160 bp
  The following strains are produced:
  BLRΔyddS
  K802ΔyddS
  WCM105ΔyddS
  MM28ΔyddS
  RV308ΔyddS
  RR1ΔyddS
  KG1005ompTΔyddS Deletion of PhoA and PhoS Procedure is similar.
  The following strains are produced:
  BLRΔphoA
  K802ΔphoA
  WCM105ΔphoA
  MM28ΔphoA
  RV308ΔphoA
  RR1ΔphoA
  KG1005ompTΔphoA
  BLRΔphoS
  K802ΔphoS
  WCM105ΔphoS
  MM28ΔphoS
  RV308ΔphoS
  RR1ΔphoS
  KG1005ompTΔphoS Example 3

Generation of Multiple Deletion Mutants

The generation of multiple mutants comprised deleting step-by-step according to the procedure described in example 2 also the other 6 identified genes in some of the strains generated in example 2.
  The following strains are produced inter alia:
  K802•oppA•fliC
  BLRΔphoAΔoppA
  BLRΔphoAΔoppAΔyddSΔphoAΔphoS
  BLRΔphoAΔyddS
  BLRΔphoAΔoppAΔyddSΔfliC
  WCM105ΔoppAΔompA
  WCM105ΔompAΔfliC
  WCM105ΔoppAΔphoA
  WCM105ΔoppAΔyddS
  WCM105ΔfliCΔyddS
  WCM105ΔoppAΔfliC
  WCM105ΔoppAΔfliCΔyddS
  WCM105ΔoppAΔfliCΔyddSΔphoA

Example 4

Characterization of Deletion Mutants With Respect to Growth

Growth of the various strains at 30° C. in LB containing 1% glucose is investigated by measuring OD at 600 nm after 24 h and 48 h of growth.

All strains exhibited normal growth, i.e. growth is not restricted compared to the starting strain. The deletions thus have no adverse effect on the viability and growth of the strains.

Table 1 depicts results of selected strains:

| Strain | OD600 (24 h) | OD600 (48 h) |
|---|---|---|
| WCM105 | 9.8 | 10.1 |
| WCM105ΔfliC | 10.0 | 10.2 |
| WCM105ΔompA | 9.8 | 10.3 |
| WCM105ΔoppA | 9.9 | 10.1 |
| WCM105ΔyddS | 9.9 | 10.4 |
| WCM105ΔphoA | 9.8 | 10.4 |
| WCM105ΔoppAΔompA | 10.1 | 10.4 |
| WCM105ΔompAΔfliC | 10.2 | 10.5 |
| WCM105ΔoppAΔphoA | 9.9 | 10.0 |
| WCM105ΔoppAΔfliCΔyddS | 10.0 | 10.2 |
| WCM105ΔoppAΔfliCΔyddSΔphoA | 10.0 | 10.1 |
| K802 | 8.8 | 12.4 |
| K802•oppA | 9.0 | 12.5 |
| K802•fliC | 8.8 | 12.4 |
| K802•oppA•fliC | 9.2 | 12.8 |

Example 5

Characterization of Deletion Mutants with Respect to Contaminating Proteins in the Supernatant In order to analyze the contaminating proteins in the supernatants of the strains of the invention, aliquots of the cultures are analyzed by SDS-PAGE and Coomassie staining. As FIG. 2 shows for a selected strain, the background proteins corresponding to the deleted genes are no longer present in the supernatant of these strains. As a result, the total amount of contaminating background bands is markedly reduced.

Example 6

Increased Specific Production of a Cyclo-Dextrin Glycosyl Transferase

Various strains, generated as described in examples 2 and 3, are employed for production of a cyclodextrin glycosyl transferase. For this purpose, the strains were transformed with pCM301 plasmid according to common methods (e.g. by means of $CaCl_2$ transformation). This plasmid contains the structural gene of Klebsiella oxytoca M5a1 cyclodextrin glycosyl transferase under the control of the tac promoter and is described in EP 0 220 714.

The strains of the invention are grown in 10 ml of LB medium containing 1% glucose at 30° C. Production of cyclodextrin glycosyl transferase is induced at OD=0.5 by adding IPTG (isopropylthiogalactoside) at 0.5 mM (final concentration).

Both total protein content (by the Bradford method) and the yield of cyclodextrin glycosyl transferase are determined in the supernatants of the strain cultures by the following activity assay:

Assay buffer: 5 mM Tris-HCl buffer>pH 6.5, 5 mM $CaSO_4.2 H_2O$

Substrate: 10% starch Noredux solution in assay buffer (pH 6.5)

Assay mixture: 1 ml of substrate solution+1 ml of centrifuged culture supernatant (5 min, 12 000 rpm)+3 ml of methanol Reaction temperature: 40° C.

Enzyme assay:
- Pre-thermostating of solutions (approx. 5 min at 40° C.)
- Addition of enzyme solution to substrate solution; rapid mixing (whirl mixer)
- Incubation at 40° C. for 3 min
- Stopping of enzyme reaction by adding methanol; rapid mixing (whirl mixer)
- Cooling of mixture on ice (approx. 5 min)
- Centrifuging (5 min, 12 000 rpm) and removing of the clear supernatant by pipetting
- Analysis of CDs produced by means of HPLC Enzyme activity: $A = G*V1*V2/(t*MG)$ (units/ml)

A=Activity

G=CD content in mg/l=assay mixture: area units×$10^4$/standard solution (10 mg/ml)/area units V1=Dilution factor/assay mixture (→5)

V2=Dilution factor/enzyme solution t=Reaction time in min (→3)

MG=Molecular weight in g/mol (CD→973)

1 unit=1 •mol of product/min.

Table 2 depicts the increased specific yield of cyclodextrin glycosyl transferase of selected strains of the invention.

| Strain (in each case with pCM301) | Total protein in supernatant (mg/l) | Cyclodextrin glycosyl transferase produced (U/ml) | Specific yield of cyclodextrin glycosyl transferase (U/mg) |
|---|---|---|---|
| WCM105 | 503 | 99 | 196.8 |
| WCM105ΔphoA | 490 | 98 | 200.0 |
| WCM105ΔfliC | 482 | 104 | 215.8 |
| WCM105ΔyddS | 498 | 99 | 198.8 |
| WCM105ΔoppA | 500 | 110 | 220.0 |
| WCM105ΔompA | 470 | 103 | 219.1 |
| WCM105ΔoppAΔompA | 461 | 101 | 219.1 |
| WCM105ΔompAΔfliC | 470 | 105 | 223.4 |

-continued

| Strain (in each case with pCM301) | Total protein in supernatant (mg/l) | Cyclodextrin glycosyl transferase produced (U/ml) | Specific yield of cyclodextrin glycosyl transferase (U/mg) |
|---|---|---|---|
| WCM105ΔoppAΔphoA | 476 | 102 | 214.3 |
| WCM105ΔoppAΔfliCΔyddS | 464 | 97 | 209.1 |
| WCM105ΔoppAΔfliCΔyddSΔphoA | 451 | 107 | 237.3 |
| K802 | 320 | 67 | 209.4 |
| K802ΔfliC | 307 | 68 | 221.5 |
| K802ΔoppA | 298 | 61 | 204.7 |
| K802ΔoppAΔfliC | 275 | 62 | 225.5 |

Example 7

Increased Specific Production of DsbG by Strains Generated According to Examples 2 and 3

7.1 Cloning of dsbG

A vector for overproducing dsbG (Swiss Prot # P77202) is constructed as follows:

PCR with chromosomal DNA from W3110 (ATCC # 27325) as template and the following primers:

```
                                    (SEQ ID NO. 23)
dsbG-fw:
GCT CTA GAG GAT CCG AAA AGG ACA AAT TAA TGT TAA

AAA AG (SEQ ID NO. 24)
dsbG-rev:
CGA ATT CTT ATT TAT TCC CCA TAA TGA TAT TAA G
```

Restriction of 783 bp PCR product with XbaI and EcoRI
Restriction of pASK-IBA3 (IBA, Göttingen, Germany) with XbaI and EcoRI
Ligation of the two DNA fragments The resulting plasmid is referred to as pASK-dsbG (3961 bp) and contains the dsbG gene including the signal sequence under the control of the tet promoter.

7.2 Increased Production of DsbG

Strains prepared according to examples 2 and 3 are transformed with pASK-dsbG plasmid according to common methods (e.g. CaCl$_2$-transformation) and the strains of the invention listed in table 3 are obtained.

The strain K802ΔoppA/pASK-dsbG was deposited under number DSM 17899 with the DSMZ (Deutsche Sammlung für Mikroorganismen und Zellkulturen GmbH, D-38142 Brunswick, Germany) according to the Budapest Treaty on Jan. 26, 2006.

The strain K802ΔfliC/pASK-dsbG was deposited under number DSM 17898 with the DSMZ (Deutsche Sammlung für Mikroorganismen und Zellkulturen GmbH, D-38142 Brunswick, Germany) according to the Budapest Treaty on Jan. 26, 2006.

The strains are grown in 10 ml of LB medium containing 1% glucose and 100 mg/l ampicillin at 30° C. Production of DsbG is induced at OD=0.5 by adding anhydrotetracycline at 0.2 mg/l (final concentration). After various periods of time, cell-free supernatant is in each case fractionated on an SDS polyacrylamide gel and analyzed after staining with Coomassie Brilliant Blue. Quantitative evaluation is carried out after scanning using a Biorad GS-800 calibrated densitometer by means of Quantity One 1-D-Analysis Software (Biorad) in comparison with a standard.

FIGS. 3 and 4 and table 3 demonstrate, for a few examples, that production of DsbG is improved in the strains of the invention compared to the starting strains.

TABLE 3

| Strain (in each case with pASK-dsbG) | Culturing time (h) | DsbG yield (mg/l) | Total protein (mg/l) | Specific dsbG production (DsbG/total protein) |
|---|---|---|---|---|
| WCM105 | 9 | 162 | 432 | 0.38 |
| WCM105 | 24 | 291 | 445 | 0.65 |
| WCM105 | 48 | 285 | 460 | 0.62 |
| WCM105 | 72 | 358 | 542 | 0.66 |
| WCM105ΔoppAΔyddSΔfliC | 9 | 428 | 420 | 1.02 |
| WCM105ΔoppAΔyddSΔfliC | 24 | 415 | 425 | 0.98 |
| WCM105ΔoppAΔyddSΔfliC | 48 | 450 | 440 | 1.02 |
| WCM105ΔoppAΔyddSΔfliC | 72 | 503 | 451 | 1.12 |
| K802 | 72 | 60 | 76 | 0.79 |
| K802ΔoppA | 72 | 59 | 74 | 0.80 |
| K802ΔfliC | 72 | 60 | 72 | 0.83 |
| K802ΔoppAΔfliC | 72 | 60 | 63 | 0.95 |

What is claimed is:

1. A microorganism strain comprising:
a gene coding for a recombinant protein, the recombinant protein to be isolated and purified after it has been secreted during fermentation; and a host gene that comprises a mutation such that the encoded host protein is not expressed or has reduced expression when compared to the host protein expression in a microorganism comprising a host gene that does not comprise the mutation, wherein the host gene does not encode a protease and encodes a host protein that is naturally secreted into a fermentation medium, wherein the recombinant protein is secreted into a fermentation medium, and wherein the strain is derived from an *Escherichia coli* strain.

2. The microorganism strain of claim 1, wherein the host protein encoded by the mutated host gene is produced and secreted in an amount which is reduced by 25 to 100% compared to production and secretion host protein in a wild-type cell.

3. The microorganism strain of claim 1,
wherein the host protein encoded by the mutated host gene is produced and secreted in an amount which is reduced by 75 to 100% compared to production and secretion of host protein in a wild-type cell.

4. The microorganism strain of claim 1,
wherein the host protein encoded by the mutated host gene is completely switched off.

5. The microorganism strain of claim 1,
wherein the host protein is selected from the group consisting of OppA, OmpA, DppA, YddS, FliC, PhoA, and PhoS.

6. The microorganism strain of claim 1, wherein the recombinant protein is a heterologous protein.

7. The microorganism strain of claim 1, wherein the strain is derived from the group consisting of BLR, WCM 105, MM28=N99=CGSC #5892, K802=CGSC #5610=WA802, RV308=ATCC 31608.

8. The microorganism strain of claim 1, wherein the gene coding for the protein to be produced is linked to a signal sequence which results in the protein to be produced being produced initially as a fusion with a signal peptide encoded by a signal sequence.

9. A microorganism strain comprising:
a gene coding for a recombinant protein, the recombinant protein to be isolated and purified after it has been secreted during fermentation; and a host gene that comprises a mutation such that the encoded host protein is not expressed or has reduced expression when compared to the host protein expression in a microorganism comprising a host gene that does not comprise the mutation, wherein the encoded host protein is selected from the group consisting of OppA, OmpA, DppA, YddS, FliC, PhoA, and PhoS, wherein the recombinant protein is secreted into a fermentation medium, and wherein the strain is derived from an *Escherichia coli* strain.

10. The microorganism strain of claim 9,
wherein the strain is derived from the group consisting of BLR, WCMI05, MM28=N99=CGSC #5892, 1£802=CGSC #5610=WAS02, RV308=ATCC 31608.

* * * * *

UNITED STATES PATENT AND TRADEMARK OFFICE
CERTIFICATE OF CORRECTION

PATENT NO. : 7,749,756 B2  Page 1 of 1
APPLICATION NO. : 11/701725
DATED : July 6, 2010
INVENTOR(S) : Susanne Leonhartsberger et al.

It is certified that error appears in the above-identified patent and that said Letters Patent is hereby corrected as shown below:

Column 26, Line 28, Claim 10:

Delete "1£802" and insert -- K802 --.

Signed and Sealed this

Twenty-eighth Day of September, 2010

David J. Kappos
*Director of the United States Patent and Trademark Office*